(12) United States Patent
Kawabata et al.

(10) Patent No.: US 11,045,168 B2
(45) Date of Patent: Jun. 29, 2021

(54) ULTRASONIC IMAGING DEVICE, AND ULTRASONIC TRANSMISSION/RECEPTION METHOD

(71) Applicant: Hitachi, Ltd., Tokyo (JP)

(72) Inventors: Kenichi Kawabata, Tokyo (JP); Hideki Yoshikawa, Tokyo (JP); Rei Asami, Tokyo (JP); Takahide Terada, Tokyo (JP); Kazuhiro Yamanaka, Tokyo (JP); Yushi Tsubota, Tokyo (JP); Wenjing Wu, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 496 days.

(21) Appl. No.: 15/762,628

(22) PCT Filed: Apr. 28, 2016

(86) PCT No.: PCT/JP2016/063392
§ 371 (c)(1),
(2) Date: Mar. 23, 2018

(87) PCT Pub. No.: WO2017/187608
PCT Pub. Date: Nov. 2, 2017

(65) Prior Publication Data
US 2018/0271480 A1 Sep. 27, 2018

(51) Int. Cl.
*A61B 8/00* (2006.01)
*A61B 8/14* (2006.01)
(Continued)

(52) U.S. Cl.
CPC ............ *A61B 8/406* (2013.01); *A61B 8/0825* (2013.01); *A61B 8/14* (2013.01); *A61B 8/4209* (2013.01);
(Continued)

(58) Field of Classification Search
CPC ........... A61B 8/0825; A61B 8/14; A61B 8/15; A61B 8/406; A61B 8/4209; A61B 8/4281;
(Continued)

(56) References Cited

U.S. PATENT DOCUMENTS 4,485,819 A * 12/1984 Igl ........................... A61B 10/00
128/660
4,545,385 A * 10/1985 Pirschel ................. A61B 10/00
128/660

(Continued)

FOREIGN PATENT DOCUMENTS

JP 5-220148 A 8/1993
JP 2007-282960 A 11/2007

(Continued)

OTHER PUBLICATIONS

International Preliminary Report on Patentability (PCT/IB/338 & PCT/IB/373) issued in PCT Application No. PCT/JP2016/063392 dated Nov. 8, 2018, including English translation of document C2 (Japanese-language Written Opinion (PCT/ISA/237)) previously filed on Mar. 23, 2018 (six pages).

(Continued)

*Primary Examiner* — Joanne M Hoffman
*Assistant Examiner* — Alexei Bykhovski
(74) *Attorney, Agent, or Firm* — Crowell & Moring LLP

(57) ABSTRACT

An ultrasonic imaging device according to the present invention includes: a container provided with an opening for inserting a target region of a subject; and a transmission/reception unit that transmits ultrasound to the target region inserted into the container filled with a liquid and receives the ultrasound that penetrates the target region or is reflected from the target region. The container has a pressure reducing unit that holds the target region in the container by reducing (Continued)

a pressure in the container of which the opening is covered with the target region. According to the present invention, since it is possible to maintain a shape close to a predetermined shape when the target region of a breast or the like is inserted into a container filled with the liquid, it is possible to measure the target region with high accuracy by transmitting and receiving ultrasound.

12 Claims, 14 Drawing Sheets

(51) Int. Cl.
*A61B 8/08* (2006.01)
*A61B 8/15* (2006.01)

(52) U.S. Cl.
CPC .......... *A61B 8/4281* (2013.01); *A61B 8/4494* (2013.01); *A61B 8/5207* (2013.01); *A61B 8/54* (2013.01); *A61B 8/543* (2013.01); *A61B 8/15* (2013.01); *A61B 8/5246* (2013.01)

(58) Field of Classification Search
CPC ... A61B 8/4494; A61B 8/5207; A61B 8/5246; A61B 8/54; A61B 8/543
See application file for complete search history.

(56) References Cited

U.S. PATENT DOCUMENTS

| | | | | |
|---|---|---|---|---|
| 5,524,636 | A | * 6/1996 | Sarvazyan | ........... A61B 1/0052 600/587 |
| 2005/0203399 | A1 | * 9/2005 | Vaezy | .................... A61B 8/001 600/439 |
| 2010/0130864 | A1 | * 5/2010 | Donnelly | .................. A61B 8/14 600/449 |
| 2012/0027276 | A1 | * 2/2012 | Chono | ...................... G06K 9/00 382/128 |
| 2014/0357998 | A1 | 12/2014 | Suzuki et al. | |
| 2016/0038123 | A1 | * 2/2016 | Duric | ....................... A61B 8/15 600/443 |
| 2017/0035361 | A1 | 2/2017 | Yamamoto | |

FOREIGN PATENT DOCUMENTS

| | | |
|---|---|---|
| JP | 2009-261611 A | 11/2009 |
| JP | 2013-116214 A | 6/2013 |
| JP | 2015-205041 A | 11/2015 |
| JP | 2016-43045 A | 4/2016 |

OTHER PUBLICATIONS

International Search Report (PCT/ISA/210) issued in PCT Application No. PCT/JP2016/063392 dated Jun. 14, 2016 with English translation (five (5) pages).
Japanese-language Written Opinion (PCT/ISA/237) issued in PCT/JP2016/063392 dated Jun. 14, 2016 (three (3) pages).

* cited by examiner

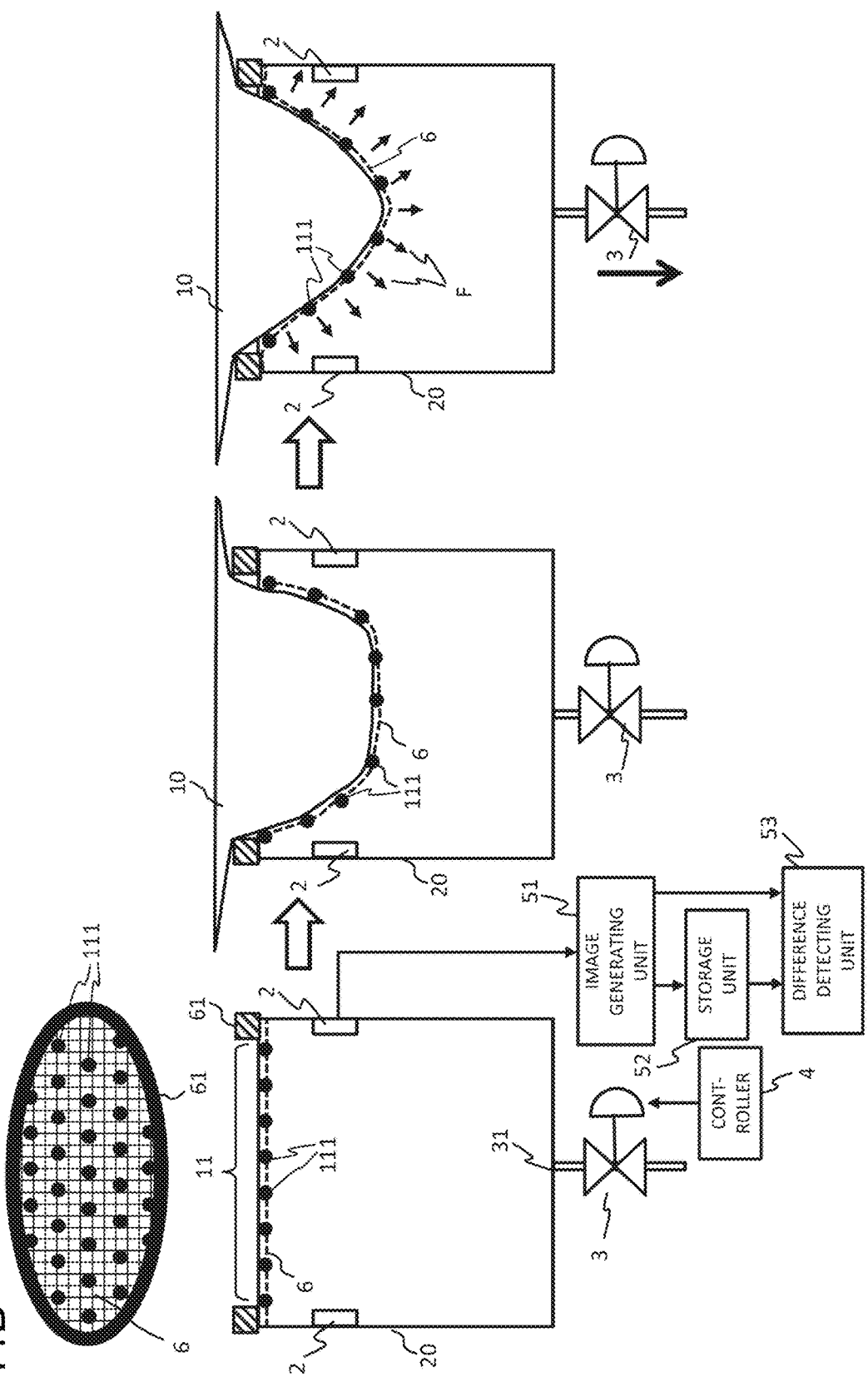

ULTRASONIC IMAGING DEVICE, AND ULTRASONIC TRANSMISSION/RECEPTION METHOD

TECHNICAL FIELD

The present invention relates to imaging ultrasound for measuring a shape characteristic of a target object in a liquid by using an ultrasonic signal.

BACKGROUND ART

There has been known an ultrasonic diagnostic apparatus that irradiates a living organ with ultrasound, acquires a reflected wave, and thereby acquires a tomogram of the living organ in a non-invasive manner. In recent years, a breast cancer screening test using an ultrasonic diagnostic apparatus comes into use. The breast cancer screening test using the ultrasonic diagnostic apparatus is generally performed by causing an ultrasound probe to move with the ultrasound probe coming into press contact with a surface of a breast of a subject and acquiring tomograms through the entire breast; however, since a breast has a complex shape and time or the like for applying a jelly-like sound coupling agent on the surface of the breast is required, time to acquire tomograms through the entire breast is required. Additionally, since image information differs due to a minute difference in strength and angle at which a probe comes into press contact with a target, a problem arises in that a difference between imaging results and a between in diagnostic results are likely to occur depending on an operator. Therefore, PTL 1 proposes an apparatus that acquires tomograms of an entire breast in a short time by immersing the entire breast in a water tank, irradiating the breast with ultrasound from a two-dimensional ultrasonic transducer array disposed on a bottom surface of the water tank, and performing two-dimensional scanning of the ultrasound.

CITATION LIST

Patent Literature

[PTL 1] JP-A-2009-261611

SUMMARY OF INVENTION

Technical Problem

In the apparatus of PTL 1, since the two-dimensional scanning is automatically performed, the strength and the angle at which a probe comes into press contact with the breast are not dependent on an operator. However, the apparatus does not ensure whether an operation is performed with the optimal strength, angle, or speed.

In addition, all of the ultrasonic diagnostic apparatuses of the related art described above are capable of acquiring tomograms; however, the tomograms are qualitative image information, and thus accuracy of diagnosis based on the image information significantly depends on skills of a doctor. In particular, in order to diagnose the presence or absence of breast cancer from a tomographic image of a breast, advanced skills are required. Since the number of doctors having the advanced skills is limited, it is difficult in practice for highly skilled doctors to perform all breast cancer screening tests of subjects. Further, even in a case where a tumor mass is found, it is not possible to easily determine whether the tumor mass is malignant cancer or a disorder that is not benign cancer with only information obtained by the apparatus of PTL 1, but a tumor mass that is not cancer but actually so-called false positive is likely to be determined as a suspected cancer.

On the other hand, as long as a use of an irradiation method or an analysis method of ultrasound can provide the appearance of a breast, a minute difference of the size or the number of internal tumor masses with time, a quantitative value of a physical property of intramammary tissue, or the, the method can assist a doctor's diagnosis. However, a breast in which there is no bone is likely to be deformed and is easily deformed when an ultrasound probe comes into press contact with the surface of the breast. In addition, even in a case of a method in which a breast is immersed in a water tank, a position and a shape of the breast are easily changed in the water tank due to a position or a direction of a subject with respect to the water tank. Therefore, it is difficult to obtain the same shape of a breast in the method of the related art when the shape is measured at different times and dates, and it is difficult to image a tomogram with high reproducibility. The tomograms of a breast, which have different shapes whenever imaging is performed, make it difficult to detect a minute difference in the appearance of the breast and an internal tumor mass with time by comparing the tomograms even in a case of the same subject.

An object of the present invention is to provide an ultrasonic imaging device that is capable of maintaining a shape close to a predetermined shape of a target region of a breast or the like when the target region is inserted into a water tank.

Solution to Problem

In order to solve the problem described above, there is provided an ultrasonic imaging device of the present invention including: a container provided with an opening for inserting a target region of a subject; and a transmission/reception unit that transmits ultrasound to the target region inserted into the container and receives the ultrasound (a penetrated wave, a reflected wave, and the like) that is scattered from the target region. The container has a pressure reducing unit that holds the target region in the container by reducing a pressure in the container of which the opening is covered with the target region.

Advantageous Effects of Invention

According to the present invention, since it is possible to maintain a shape close to a predetermined shape when the target region of a breast or the like is inserted into a water tank, it is possible to measure the target region with high accuracy by transmitting and receiving ultrasound.

BRIEF DESCRIPTION OF DRAWINGS

FIG. 11A is a diagram illustrating an overview of a configuration of an ultrasonic imaging device of a third embodiment which has the mesh 6 provided with a marker 11, FIG. 11B is a diagram illustrating a state of the ultrasonic imaging device having the mesh 6 provided with the marker 11 in which a target region of a subject is inserted into a container, FIG. 11C is a diagram illustrating a state of the ultrasonic imaging device having the mesh 6 provided with the marker 11 in which a pressure in the container is reduced, and FIG. 11D is a perspective view of the mesh 6 provided with the marker 11.

DESCRIPTION OF EMBODIMENTS

Hereinafter, an embodiment of the present invention will be described with reference to the figures. In the figures to which the embodiments are described with reference, the same names and reference signs are assigned to elements having the same functions, and thus the repeated description thereof is omitted.

First Embodiment

Figure 1:
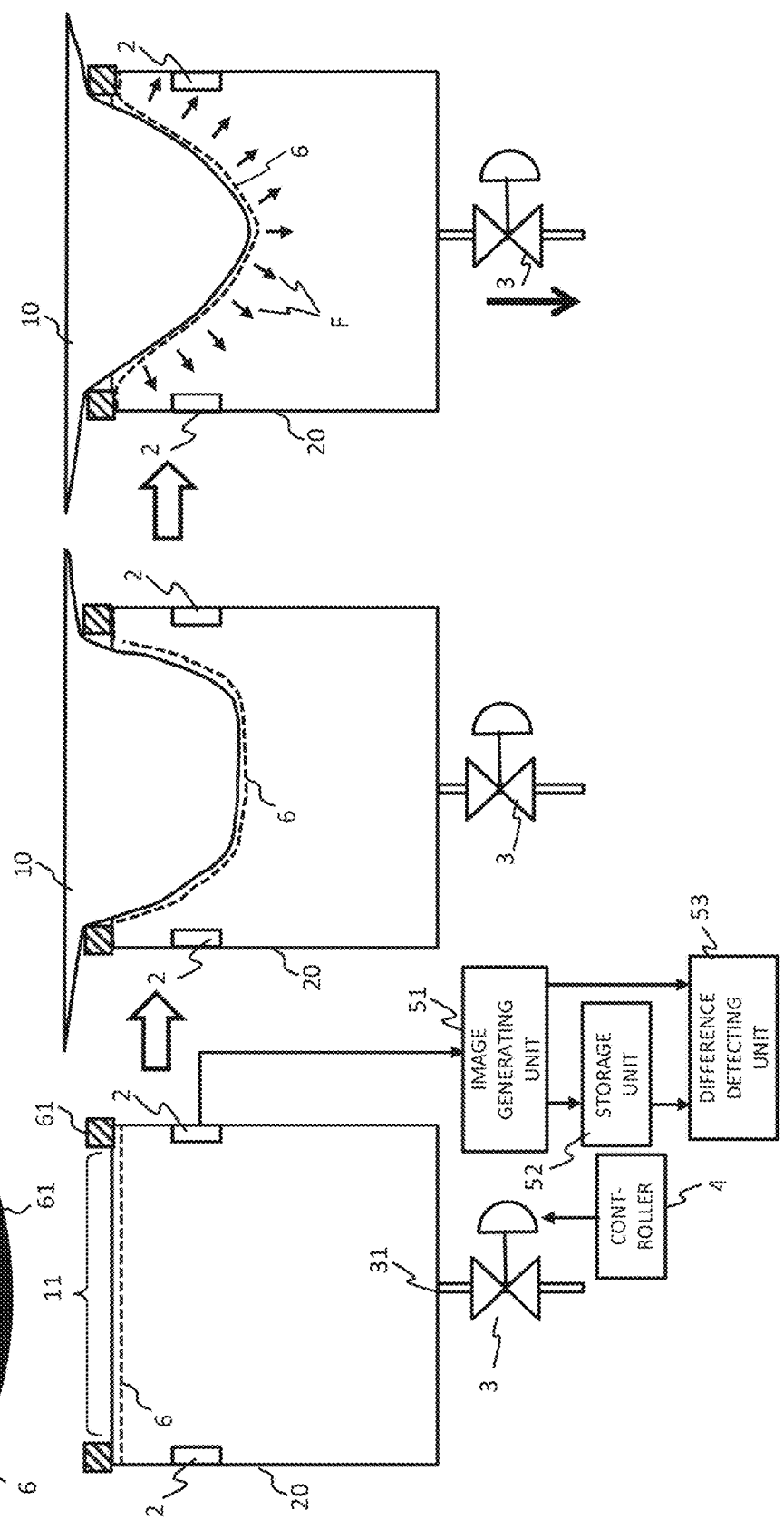
FIG. 1A is a diagram illustrating an overview of a configuration of an ultrasonic imaging device of a first embodiment before a target region of a subject is inserted.
FIG. 1B is a diagram illustrating a state of the ultrasonic imaging device in which the target region of the subject is inserted into a container.
FIG. 1C is a diagram illustrating a state of the ultrasonic imaging device in which a pressure in the container, into which the target region of the subject is inserted, is reduced.
FIG. 1D is a perspective diagram of a mesh 6 of the ultrasonic imaging apparatus.

A configuration of an ultrasonic imaging device (ultrasound transmitting/receiving device) of the embodiment is described with reference to FIGS. 1(a) and 1(b). FIG. 1(a) is a diagram illustrating an overview of the configuration of the ultrasonic imaging device before a target region of a subject is mounted, FIG. 1(b) is a diagram illustrating a state in which the target region of the subject is inserted into a container, FIG. 1(c) is a diagram illustrating a state in which a pressure in the container, into which the target region of the subject is inserted, is reduced.

As illustrated in FIGS. 1(a) and 1(b), the ultrasonic imaging device of the embodiment includes a container 20 provided with an opening 11 for inserting the target region of the subject and a transmission/reception unit 2 that transmits ultrasound to a target region 10 inserted into the container 20 and receives ultrasound (a penetrated wave penetrating the target region, a reflected wave reflected from the target region, and the like) that is scattered from the target region. The container 20 includes a pressure reducing unit 3. A pressure in the container 20, of which the opening 11 is covered with the target region 10, is reduced by the pressure reducing unit 3, and thereby it is possible to hold the target region 10 while controlling the surface state of the target region 10 in the container 20 as illustrated in FIG. 1(c).

In other words, the pressure reducing unit 3 reduces the pressure in the container 20 in a state in which the target region 10 blocks the opening 11 of the container 20. In this manner, the pressure in the container 20 becomes the negative pressure with respect to external pressure, and thus a pulling force F is uniformly applied to a surface of the target region 10 in a normal direction. In this manner, a surface shape of the target region 10 is deformed into a shape formed by a balance the uniform force F with resistance force of a skin or internal tissue of the target region 10, and the shape is maintained. For example, in a case where the tissue of the target region 10 has uniform elasticity, the surface shape becomes smooth and approaches a predetermined shape, and the shape is maintained in this state. In a case where the elasticity of the tissue of the target region 10 is locally different from that on the periphery, strain is locally generated on the surface shape due to a difference in elasticity, and the shape is maintained in this state.

Hence, in a case where the target region 10 is a breast, for example, the ultrasonic imaging device of the embodiment is capable of decreasing an influence of a position or a direction of the breast on a shape of the breast when the breast is inserted into the container by reducing pressure and is capable of maintaining the shape of the breast which is close to a predetermined shape.

It is desirable that the space in the container 20 is filled with a liquid. It is desirable that the liquid has a low attenuation rate of the ultrasound. In particular, it is preferable that, in order to decrease refraction of the ultrasound when the ultrasound in the liquid is incident to the target region 10, a sound speed of the ultrasound in the liquid is approximate to that of the internal tissue of the target region 10. For example, water is used as the liquid. The pressure reducing unit 3 reduces the pressure in the container 20 by discharging, to an outside of the container 20 from a through-hole 31 provided in the container 20, a part of the liquid, with which the space in the container 20 is filled. For example, it is possible to employ, as the pressure reducing unit 3, a configuration in which a valve connected to the through-hole 31 is used and the liquid is discharged outside the container 20 by own weight of the liquid or a configuration in which the liquid in the container 20 is discharged by a pump or the like via a valve.

A controller 4 that controls an operation of the pressure reducing unit 3 may be connected to the pressure reducing unit 3. In this case, the controller 4 detects the shape of the target region 10 after causing the pressure reducing unit 3 to be operated so as to reduce the pressure in the container 20 by predetermined pressure and determines whether or not the shape reaches a predetermined shape. As a method of determining whether the shape reaches the predetermined shape, a method, in which the controller 4 detects both of a diameter of the target region 10 at a predetermined depth from the opening 11 and a length from the opening 11 to the distal end of the target region 10 and determines that the shape reaches the predetermined shape when a ratio of the diameter and the length is within a predetermined range.

Instead of the diameter of the target region 10 at the predetermined depth from the opening 11, a diameter of the opening 11 or a predetermined value may be used.

The controller 4 is capable of causing the pressure reducing unit 3 to further reduce the pressure in the container 20 in a case where the shape of the target region 10 does not reach the predetermined shape. In this manner, it is possible to obtain a shape of the target region 10 which is close to the predetermined shape.

The controller 4 may be configured to cause the transmission/reception unit 2 to transmit ultrasound toward the target region 10 and to cause the transmission/reception unit 2 to receive a reflected wave or a penetrating wave from the target region 10, in order to detect the shape of the target region 10. The controller 4 is capable of detecting an external shape of the target region 10 by processing a received signal obtained by receiving ultrasound by the transmission/reception unit 2. The transmission/reception unit 2 may move in the container 2 and may transmit and receive the ultrasound at a plurality of positions. In this manner, since it is possible to detect the shape of the target region 10 by using the transmission/reception unit 2, there is no need to prepare another configuration for detecting a shape, and it is possible to simplify the configuration of the device. However, the present invention is not limited to this configuration, it is also possible to employ a configuration in which a sensor or the like that detects the shape of the target region 10 is separately provided. For example, it is possible to use a sensor, a camera, or the like that optically detects the shape of the target region 10.

It is desirable that the ultrasonic imaging device of the embodiment further includes: an image generating unit 51 that calculates an image showing the shape or a sectional structure of the target region 10 based on the received signal obtained by transmitting the ultrasound by the transmission/reception unit 2 and, then, receiving the reflected wave and/or the penetrating wave from the target region 10 or that calculates an image of a physical property distribution such as a sound speed distribution/attenuation distribution; a storage unit 52 that stores the calculated image; and a difference detecting unit 53 that obtains a difference by comparing the image that is currently calculated by the image generating unit 51 to an image calculated in the past by transmission and reception of ultrasound. In the embodiment, since the target region 10 is maintained to have the shape close to the predetermined shape, the shape close to the predetermined shape is maintained whenever the imaging is performed even when abreast that does not have a bone and is likely to be deformed is the target region 10. In this manner, the difference detecting unit 53 is capable of comparing images obtained by transmission and reception of the ultrasound in the present and in the past so as to obtain a difference in shape, internal tumor mass, or the like with high accuracy. The difference information is provided to a user, and thereby it is possible to assist the user or a doctor in diagnosis.

In addition, it is possible to dispose an extensible mesh 6 in the container 20 such that the opening 11 is covered with the extensible mesh. In this case, the target region 10 is inserted into the container 20 from the opening 11 so as to push the extensible mesh 6 into the space in the container 20, and the mesh 6 comes into close contact with the surface of the target region 10 (refer to FIGS. 1(b) and 1(c)). It is preferable that the mesh 6 is made of a material having low sound attenuation. For example, it is possible to use polyurethane. In addition, since the liquid passes through net meshes, the mesh 6 is unlikely to interfere with incidence and emission of the ultrasound to and from the target region 10 and is unlikely to influence an image of the target region 10. A size of the net mesh of the mesh 6 may be a size to the extent that bubbles of the target region 10 can pass through the net mesh. For example, the mesh 6 having a net mesh size of 1 mm to 10 mm is used. In addition, it is desirable that the mesh 6 is attachable to and detachable from the opening 11. This is preferable because the mesh 6 is attachable and detachable and thereby it is possible to replace the mesh 6 whenever the subject is changed. In addition, in a case where the pressure reducing unit 3 reduces the pressure in the container 20, the breast is deformed and is held by feeling a pressure difference via the mesh 6 without being separated from the mesh 6.

Figure 2:
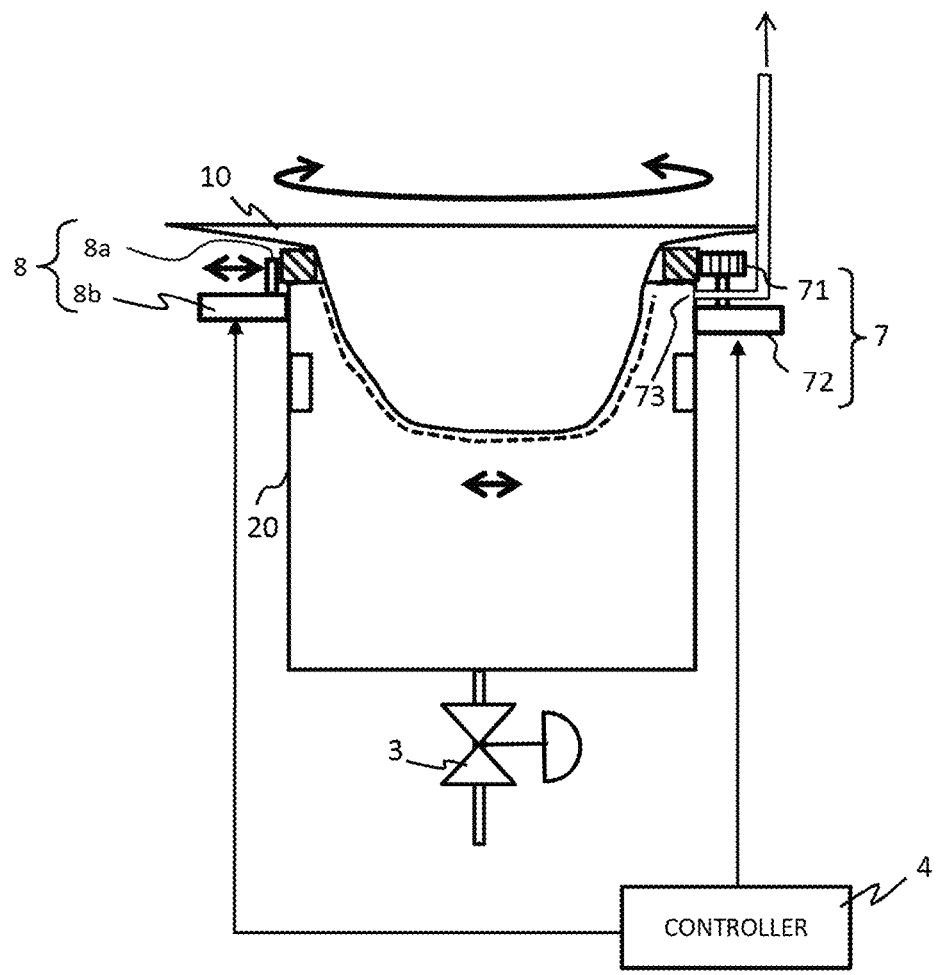
FIG. 2 is a diagram illustrating a configuration of the ultrasonic imaging device of the first embodiment which includes a rotating mechanism 7 that rotates the mesh 6.

FIG. 1(d) illustrates a perspective diagram of the mesh 6, and FIG. 2 illustrates the ultrasonic imaging device which includes a rotating mechanism 7 that rotates the mesh 6. As illustrated in FIG. 1(d), it is desirable that the mesh 6 has a configuration in which a mesh frame 61 holds the periphery of the mesh. In addition, it is desirable that the mesh 6 is attachable to and detachable from the mesh frame 61. For example, whenever abreast is inserted into the container 20 or for each subject, the mesh is replaced with a new mesh 6. The mesh frame 61 may be configured to be attachable to and detachable from the ultrasonic imaging device, and the mesh 6 may be replaced for each mesh frame 61 (the mesh frame 61 and the mesh 6 together) each time of replacement of the mesh 6. In addition, the ultrasonic imaging device further includes the rotating mechanism 7 that rotates the mesh frame 61 along the periphery of the opening 11 of the container 20. In this manner, it is possible to rotate the mesh 6 in a state in which the mesh 6 comes into close contact with the target region 10, and it is possible for the mesh 6 to rub the surface of the target region 10. In this manner, even in a case where the inside of the container 20 is filled with the liquid and bubbles are attached to the surface of the target region 10, it is possible for the mesh 6 to rub off and remove the bubbles from the surface of the target region 10. When the bubbles are attached to the target region 10, the ultrasound is reflected from an interface between the liquid and the bubble or frequency components are increased. Therefore, interference in capturing an image of the shape or the cross section of the target region 10 with high accuracy occurs, in some cases; however, it is possible to perform the capturing with high accuracy by rotating the mesh 6 and removing the bubbles in the embodiment. It is desirable that a through-hole 73 for releasing, to the outside, the bubbles that are rubbed from the target region 10 and float is provided on an upper side of the container 20.

For example, the rotating mechanism 7 of the mesh frame 61 can be configured to include a gear provided on an outer circumference of the mesh frame 61, a driving gear 71 intermeshing with the gear, and a motor 72 that rotatably drives the driving gear 71.

The controller 4 that controls an operation of the rotating mechanism may be connected to the rotating mechanism 7 as illustrated in FIG. 2. The controller 4 detects whether or not bubbles are present on the surface of the target region 10 and causes the rotating mechanism 7 to rotate the mesh frame 61 in a case where an amount of bubbles, which is equal to or larger than a predetermined amount, is present on the surface of the target region 10, and thereby the bubbles are removed. A rotating direction may be one direction; however, it is possible to remove the bubbles with high efficiency in a case of including a reciprocating motion during rotation or at the time of the end of the rotation.

The controller 4 may have any configuration of detecting the bubbles; however, it is possible to employ a configuration in which bubbles on the surface of the target region 10 is detected, based on a received signal obtained by causing the transmission/reception unit 2 to transmit the ultrasound to the target region 10 and to receive the reflected wave. For example, it is possible to employ a configuration in which the shape of the target region 10 is obtained from the received signal and the presence of the bubbles is determined in a case where a value of unevenness of the surface is equal to or larger than a predetermined value, a configuration in which the presence of bubbles is determined in a case where the signal strength on an interface between the target region 10 and the liquid is equal to or higher than that of another region of the target region 10 by a predetermined strength, or a configuration in which a ratio of harmonic components to fundamental components of the ultrasound included in the received signal and the presence of an amount of bubbles which is equal to or larger than a predetermined amount is determined in a case where the ratio of the harmonic component is equal to or higher than a predetermined ratio.

In addition, the ultrasonic imaging device may further include a moving mechanism 8 that causes the mesh frame 61 to move in at least one direction in a plane of the opening 11 of the container 20 as illustrated in FIG. 2. For example, the moving mechanism 8 includes an engagement portion 8a that engages with an edge of the mesh frame 61 and a drive unit 8b that moves the mesh frame 61 by moving the engagement portion 8a in at least one direction in the plane of the opening 11. For example, the engagement portion 8a is configured to have a distal portion provided with a projecting portion that engages with a recessed portion provided in the edge of the mesh frame 61. The engagement portion 8a is configured to be projectable and retractable. In this manner, while the rotating mechanism 7 rotates the mesh frame 61, the engagement portion 8a is lowered to a retraction position by the drive unit 8b such that the engagement portion does not interfere with the mesh frame, and is lifted by the drive unit 8a so as to engage with the edge of the mesh frame 61 when the moving mechanism 8 moves the mesh frame 61.

In a case where the position of the target region 10 (for example, a position of the distal end of the breast) is shifted from a desired position, the moving mechanism 8 moves the mesh frame 61 in a reverse direction to a shifting direction, and thereby the moving mechanism 8 is capable of correcting the shift of the position of the target region 10. In addition, the controller 4 may control the moving mechanism 8. The controller 4 obtains a positional shift of the target region 10 with respect to the container 20 and causes the moving mechanism 8 to move the mesh frame 61 in a case where an amount of the positional shift is larger than a predetermined range. For example, the controller 4 obtains the shape of the target region 10, obtains a position of a predetermined region (for example, the distal end of the breast) of the obtained shape, and causes the moving mechanism 8 to move the mesh frame 61 in a case where the position is shifted from the predetermined position (the center of the opening 11) by a distance equal to or larger than a predetermined distance. As a method in which the controller 4 obtains the shape of the target region 10, similar to the controller 4, the transmission/reception unit 2 may be used or it is possible to use a sensor or a camera that detects the shape of the target region 10.

Second Embodiment

Figure 3:
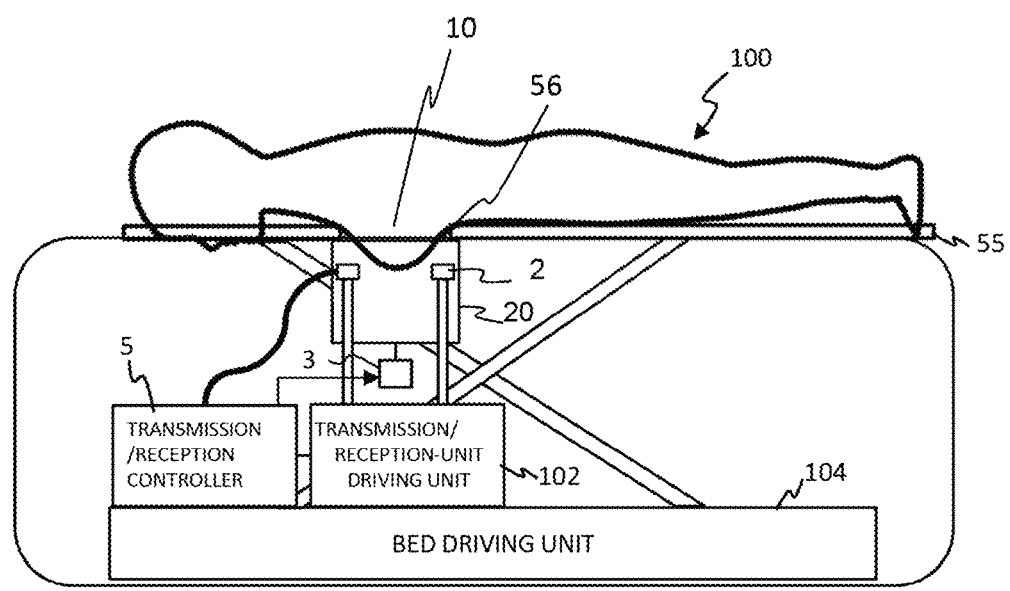
FIG. 3 is a sectional diagram illustrating an entire configuration of an ultrasonic imaging device of a second embodiment.
Figure 4:
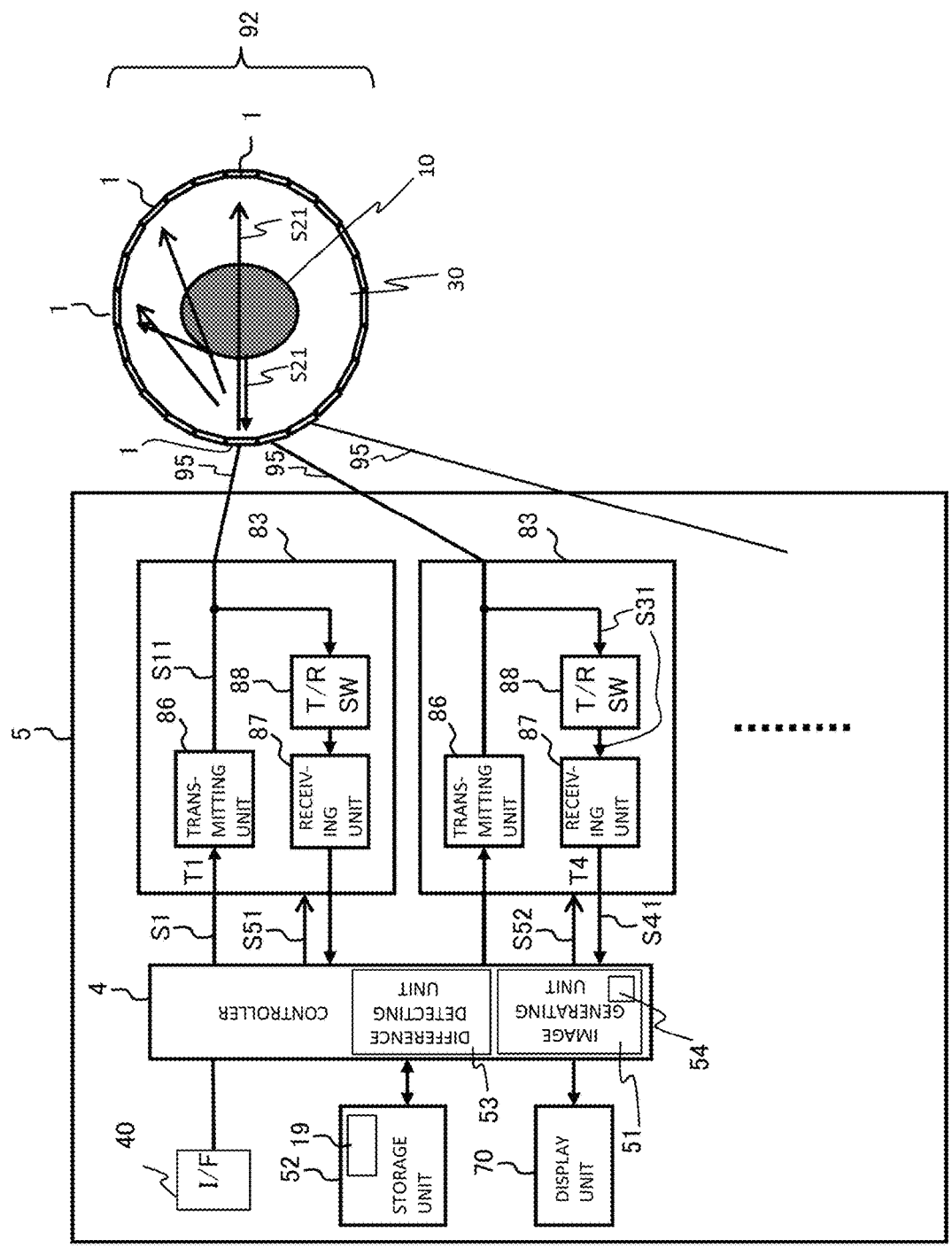
FIG. 4 is a block diagram illustrating a configuration of a transmission/reception controller 5 of the second embodiment.
Figure 5:
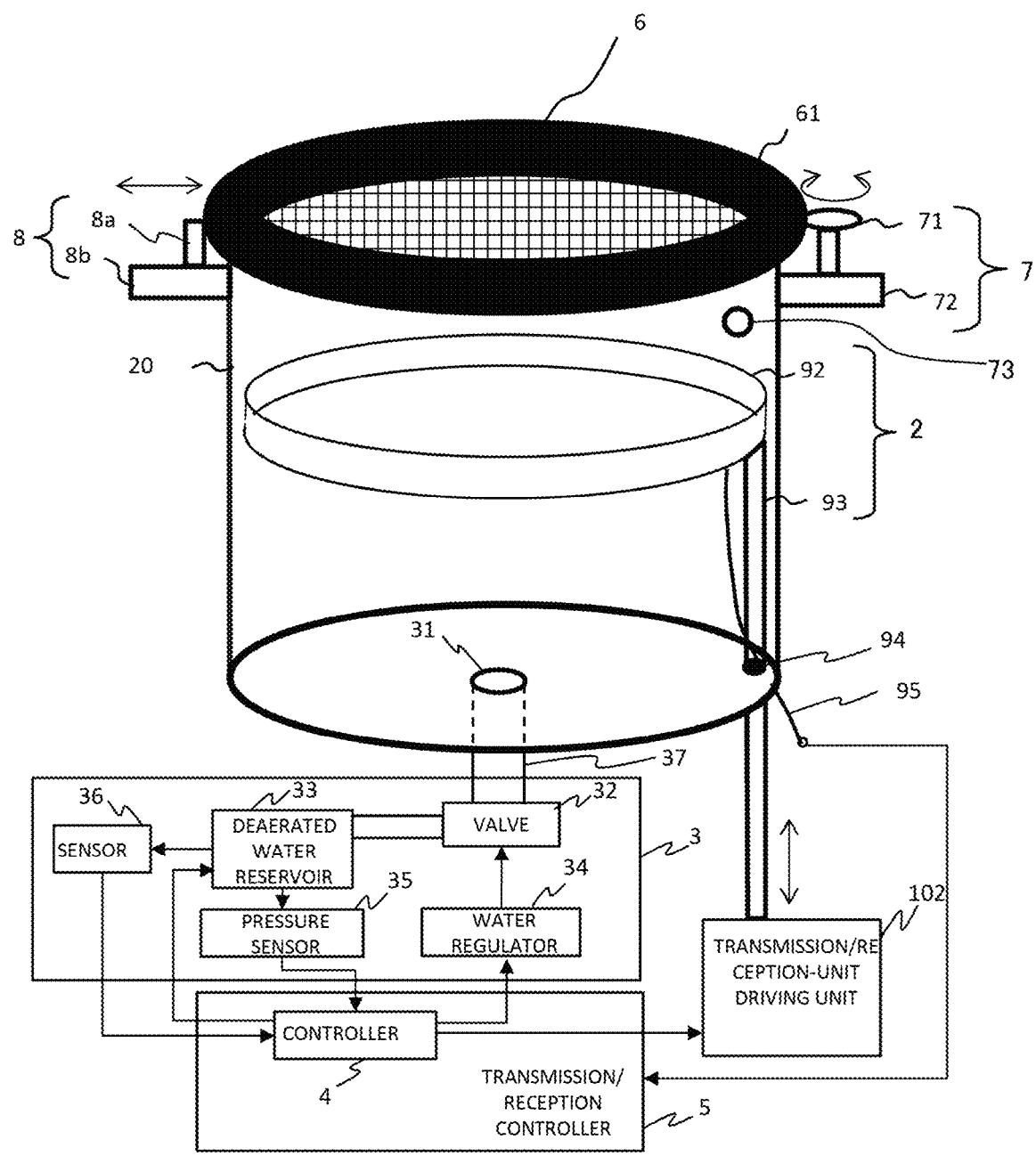
FIG. 5 is a diagram illustrating a container 20 and a control system of the second embodiment.

An ultrasonic imaging device of the second embodiment is described with reference to FIG. 3 or the like. The ultrasonic imaging device of the second embodiment is an device suitable for acquiring an image or the like which assists breast cancer screening. FIG. 3 is a sectional diagram illustrating an entire configuration of the ultrasonic imaging device of the embodiment. FIG. 4 is a block diagram illustrating configurations of the transmission/reception unit 2 and a transmission/reception controller 5. FIG. 5 is a diagram illustrating the container 20 and a control system.

As illustrated in FIG. 3, the ultrasonic imaging device of the embodiment includes abed 55 on which a subject 100 is mounted, the container 20 provided with the opening 11, the pressure reducing unit 3, the transmission/reception unit 2 of ultrasound, the transmission/reception controller 5, a transmission/reception-unit driving unit 102, and a bed driving unit 104.

The bed 55 is provided with an opening 56 for inserting the target region 10 of the subject. The container 20 is disposed under the opening 56 such that the opening 11 of the container 20 is identical with the opening of the bed 55. In the embodiment, the container 20 has a circular cylinder shape. In the embodiment, the inside of the container 20 is filled with deaerated water. Hereinafter, the container 20 is referred to as a water tank 20.

As illustrated in FIG. 5, the mesh 6 described in the first embodiment is supported by the mesh frame 61 and is disposed on the opening 11 of the water tank 20. In addition, the gear provided on the outer circumference of the mesh frame 61, the driving gear 71 intermeshing with the gear, and the motor 72 that rotatably drives the driving gear 71 are disposed, as the rotating mechanism 7 of the mesh frame 61, on a side surface of the water tank 20. In addition, the moving mechanism 8 that causes the mesh frame 61 to move in at least one direction in a plane of the opening 11 of the water tank 20 is disposed on a side surface of the water tank 20. The moving mechanism includes the engagement portion 8a and the drive unit 8b described in the first embodiment. In addition, the through-hole 73 for releasing bubbles is provided on the upper side of a side surface of the water tank 20.

The transmission/reception unit 2 has a ring-shaped transducer array 92 disposed in the water tank 20 and a moving mechanism 93 that moves the ring-shaped transducer array 92 in the water tank 20 in a direction along the central axis of the opening 11. The ring-shaped transducer array 92 is disposed along the inner wall of the water tank 20 having the circular cylinder shape and transmits and receives the ultrasound to and from the target region 10 disposed in the water tank 20. For example, the moving mechanism 93 uses a rod-shaped support tool having a front end to which the ring-shaped transducer array 92 is fixed. The front end of the rod-shaped support tool is pulled to the outside from the bottom surface of the water tank 20 and is connected to the transmission/reception-unit driving unit 102. The transmission/reception-unit driving unit 102 includes a motor or the like and moves the rod-shaped drive unit 102 in parallel with the central axis of the water tank 20, thereby vertically moving the ring-shaped transducer array 92 along the central axis in the water tank 20. The bottom surface of the water tank 20 is provided with a mechanism of a through-hole 94, packing, and the like for pulling the rod-shaped support tool to the outside while airtightness is maintained.

The moving mechanism 93 and the transmission/reception-unit driving unit 102 are not limited to a combination of the rod-shaped support tool, the motor, and the like, and any mechanism and a drive unit may be used as long as the mechanism and the drive unit are capable of moving the ring-shaped transducer array 92. For example, it is possible to use a rack and pinion as the moving mechanism 93.

A signal line 95 is connected to each of a plurality of transducers 1 that configure the ring-shaped transducer array 92. The signal line 95 is pulled to the outside of the water tank from the through-hole 94 and is connected to the transmission/reception controller 5. A transmission signal is delivered from the transmission/reception controller 5 to the transducers 1 via the signal lines 95 during the transmission of the ultrasound, and received signals received by the transducers 1 are delivered to the transmission/reception controller 5 via the signal lines 95 during the reception of the ultrasound.

The shape of the transducer array 92 is not limited to the ring shape, and any shape may be employed as long as it is possible to transmit the ultrasound to the target region 10 of the subject 100 and to receive penetrating waves and/or reflected waves thereof by using the shape. The transducer array may be divided into a plurality of arrays.

As illustrated in FIG. 5, the pressure reducing unit 3 includes the through-hole 31 provided in the bottom surface of the water tank 20, a tube 37 having one end connected to the through-hole 31, an on-off valve 32 provided on a position of the tube 37, a deaerated water reservoir 33 connected to the other end of the tube 37, a pressure sensor 35 that detects pressure of water in the deaerated water reservoir 33, and a sensor 36 that detects bubbles level or a dissolved oxygen level and a water temperature of the water in the deaerated water reservoir 33. The water regulator 34 opens and closes the on-off valve 32 so as to discharge water to the outside by a predetermined amount from the water tank 20 under control of the controller 4 in the transmission/reception controller 5. The pressure sensor 35 detects the pressure of the water in the deaerated water reservoir 33 and outputs the detection result to the controller 4. The controller 4 receives, from the sensor 36, detection results of bubbles level or the dissolved oxygen level and the water temperature of the water in the deaerated water reservoir 33 and operates a deaerating function installed in the deaerated water reservoir 33 such that the deaeration is performed when the dissolved oxygen level of the water is higher than a predetermined value. In addition, the deaerated water reservoir 33 includes a pump function (not illustrated) and increase the pressure of the water in a state in which the valve 32 is opened, thereby making it possible to inject the water in the deaerated water reservoir 33 into the water tank 20. In addition, the deaerated water reservoir 33 includes a water temperature adjusting function (not illustrated). An operation of the pressure reducing unit 3 will be described below in detail.

The transmission/reception controller 5 includes a plurality of transmitting/receiving circuits 83 connected to respective transducers 1 configuring the transducer array 92, the controller 4, the storage unit 52, and the display unit 70.

As illustrated in FIG. 4, the transmitting/receiving circuit 83 includes a transmitting unit 86, a receiving unit 87, and a transmitting/receiving switch (T/R SW) 88 that switches transmission and reception. One transmitting/receiving circuit 83 is connected to one transducer 1, and the transmitting/receiving circuits 83 are capable of individually transmitting and receiving ultrasonic signals. The controller 4 is capable of outputting different signals such as control signals S51 and S52 to the transmitting/receiving circuits 83 so as to perform different control. For example, the controller 4 is capable of causing the transmitting/receiving circuit 83, to which the control signal S51 of instructing transmission is input, to perform a transmission operation and causing the transmitting/receiving circuit 83, to which a control signal S52 of instructing reception is input, to perform a reception operation.

For example, the transmitting unit 86 is configured to have an amplifier and amplifies an electric signal S1 input from the controller 4 to predetermined strength, thereby generating a transmission signal S11 and outputting the signal to the transducer 1 via the signal line 95. The transducer 1 includes a structure of a matching layer, an acoustic lens, or the like, and converts the transmission signal S11 received from the transmitting unit 86 into an ultrasonic signal S21 so as to emit (transmit) the ultrasonic signal. The sound pressure of the ultrasonic signal S21 emitted from the transducer 1 is changed depending on the signal strength of the transmission signal S11 delivered to the transducer 1. The signal strength of the transmission signal S11 that is generated by the transmitting unit 86 is set in response to the control signal S51.

The emitted ultrasonic signal S21 passes through a space 30 in the water tank 20, penetrates the target region 10, or is reflected from the target region 10 so as to reach another transducer 1. The transducer 1 converts the reaching ultrasonic signal S21 into a received signal S31 that is the electric signal and outputs the received signal to the receiving unit 87 via the signal line 95 and the transmitting/receiving switch 88. For example, the receiving unit 87 is configured to include an amplifier, a filter, and an analog-to-digital converter, amplifies the electric signal (received signal S31) output by the transducer 1, reduces noise out of a predetermined frequency bandwidth, quantizes the noise, generates an amplified received signal S41, and outputs the amplified received signal to the controller 4. A gain of the amplifier, a constant of the filter, or the like of the receiving unit 87 is set in response to the control signal S52. The strength of the electric signal of the received signal S31 that is emitted from the transducer 1 is changed depending on the sound pressure of the ultrasonic signal S21 that is received by the transducer 1.

The transmitting/receiving switch 88 cuts the connection between the receiving unit 87 and the transducer 1 during the transmission operation and is short-circuited during the reception operation. In this manner, the receiving unit 87 is prevented from being broken due to the transmission signal S11 having a high voltage that is output from the transmitting unit 86 to the transducer 1 during the transmission operation.

The controller 4 includes the image generating unit 51, in which a computing unit 54 is installed, and the difference detecting unit 53. The controller 4 includes a central processing unit (CPU) and a memory in which a program is stored in advance and the CPU reads and executes the program. In this manner, software realizes operations of flowcharts, to be described below, of the functions of the computing unit 54, the image generating unit 51, and the difference detecting unit 53, and the controller 4 itself. The controller 4 is not limited to a configuration of realizing the functions by the software, and a part or the entirety of the controller 4 can be configured of hardware such as a custom integrated circuit (IC) of an application specific integrated circuit (ASIC) or a programmable IC of a field-programmable gate array (FPGA).

The computing unit 54 computes the obtained amplified received signal S41 by using a parameter value that is stored in a parameter storing unit 19, thereby measuring the shape of the target region 10 disposed in the space 30 and a physical property value such as a sound speed or attenuation of the ultrasonic signal S21. For example, the ultrasonic signal S21 transmitted from a certain transducer 1 passes (is propagated) through the space 30 via a predetermined route while penetrating the target region 10 or being reflected from the surface of the target region 10 and an end surface of an internal structure, and the ultrasonic signal is received by another transducer 1. The computing unit 20 calculates a time taken for the ultrasonic signal S21 to be propagated in the space 30 (an ultrasound propagating time) by using the parameter value that is stored in the parameter storing unit 19 and divides a distance between two transducers 1 by the calculated propagating time, thereby making it possible to obtain a sound speed of the target region 10. Specifically, the computing unit 54 calculates a time taken from outputting the signal S1 to the transmitting unit 86 that has generated the transmission signal S11 to receiving the amplified received signal S41 from the receiving unit 87 that has received the received signal S31 (a signal delay time) and subtracts a signal response time or the like of the transmitting/receiving circuits 83, thereby calculating a time taken from outputting the ultrasonic signal from the transducer 1 to inputting the ultrasonic signal to another transducer 1 (an ultrasound propagating time). The computing unit 54 calculates the distance between two transducers 1 from a positional coordinate in the transducer array 92 of the transducers 1. The computing unit 54 obtains the sound speeds in a plurality of different propagating routes and computes a matrix, or the like while changing the transducer 1 that emits the ultrasonic signal S21, thereby making it possible to calculate a sound speed distribution of the target region 10. In addition, it is possible to calculate another physical property value based on the sound speed.

In addition, the computing unit 54 is capable of calculating the signal attenuation in the space 30 from the strength of the amplified received signal S41. The signal attenuation is obtained for each of the plurality of different propagating routes, and thereby it is possible to calculate the attenuation distribution of the target region 10.

Further, the computing unit 54 calculates a time taken for the ultrasonic signal S21 emitted from the transducer 1 to be reflected from the surface of the target region 10 and, then, to be input to another transducer 1, thereby, making it possible to calculate the surface position of the target region 10. The surface position of the target region 10 in the plurality of propagating routes is calculated while changing the transducer 1 that emits the ultrasonic signal S21, and thereby it is possible to obtain the shape of the target region 10.

The storage unit 52 stores setting in association with a transmission/reception operation of the transmitting/receiving circuit 83 or information such as a signal waveform of the electric signal S1 that is output to the transmitting unit 86. In addition, the parameter storing unit 19 of the storage unit 52 stores a signal response time of the transmitting/receiving circuit 83 which has been obtained in advance or a value of the positional coordinate or the like in the transducer array 92 of the transducers 1. In addition, the storage unit 52 appropriately stores a waveform of the amplified received signal S41, the ultrasound propagating time, and measurement results such as the shape/sound speed/attenuation of the target region 10.

The image generating unit 51 generates an image of the shape/sound speed distribution/attenuation distribution, or the like of the target region 10 which is calculated by the computing unit 54, and the image is displayed on the display unit 70.

The difference detecting unit 53 reads data or an image of the shape/sound speed distribution/attenuation distribution of the target region 10 of the same subject 100 in the past which has been stored in the storage unit 52, compares the data or the image of the shape/sound speed distribution/attenuation distribution of the target region 10 which is calculated by the computing unit 54 in the current measurement, and detects a difference therebetween. The difference detecting unit 53 displays the detection results on the display unit 70.

Hereinafter, the operation of the ultrasonic imaging device of the embodiment will be described in detail. FIGS. 6 to 9 are flowcharts illustrating operations of the controller 4. FIG. 10 illustrates examples of a display screen of the display unit 70. For example, the controller 4 includes the CPU and the memory described above and the CPU reads the program in the memory so as to execute the program, and thereby the following operation is realized.

Figure 10A:
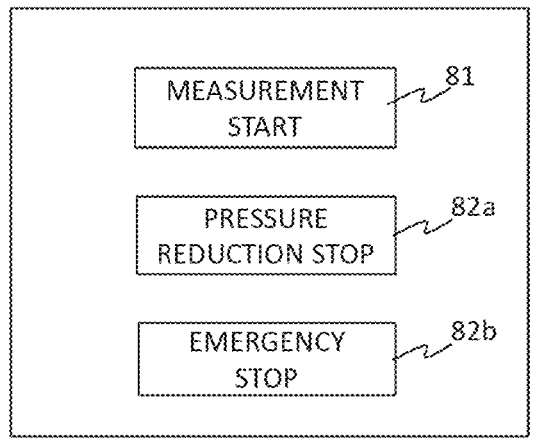
FIGS. 10A to 10C illustrate examples of a display screen of a display unit 70 of the second embodiment.

First, the controller 4 displays an operating screen illustrated in FIG. 10(a) on the display unit 70, controls the water regulator 34 and the deaerated water reservoir 33 when a user presses a measurement start button 81, opens the valve 32, and injects the deaerated water into the water tank 20 from the deaerated water reservoir 33 by a predetermined amount (Steps 601 and 602). Then, the controller 4 detects a height of a water surface by transmitting and receiving the ultrasound (Step 603). Specifically, the controller 4 transmits the signal S1 to the transmitting units 86 of one or more transmitting/receiving circuits 83 so as to generate the transmission signals S11 and instructs the computing unit 54 to receive the amplified received signal S41 from the receiving unit 87 of another transmitting/receiving circuit 83. In this manner, the transmission signals S11 are delivered to one or more transducers 1 such that the ultrasonic signals S21 are transmitted, and another transducer 1 receives the ultrasonic signal S21 reflected from the water surface of the deaerated water. The computing unit 54 processes the received amplified received signal S41, detects the reflected signal from the water surface of the deaerated water, calculates a distance of the water surface with respect to the transducer array 92, and detects the height of the water surface of the current deaerated water from a relationship between the current position of the transducer array 92 and the distance.

In a case where the height of the water surface of the deaerated water which is detected in Step 603 is not present within a setting criterion, the controller 4 adjusts an amount of water (Steps 604 and 605). In other words, the controller 4 controls the water regulator 34 and the deaerated water reservoir 33 and adds or reduces water by a predetermined amount, and a procedure returns to Step 603. In a case where the height of the water surface of the deaerated water which is detected in Step 603 is within the setting criterion, the controller 4 receives the temperature of the deaerated water from the sensor 36 and determines whether or not the water temperature is within the setting criterion (Step 606). In a case where the water temperature is out of the setting criterion, the controller 4 adjusts the water temperature (Step 607). In other words, the controller 4 instructs the deaerated water reservoir 33 to operate a temperature adjusting function and performs heating or cooling. In a case where the water temperature is within the setting criterion, the controller 4 receives the dissolved oxygen level from the sensor 36 and determines whether or not the dissolved oxygen level is within a setting criterion (Step 608). In a case where the dissolved oxygen level is equal to or higher than a set value, the controller 4 operates a deaerating function of the deaerated water reservoir 33 and adjusts the dissolved oxygen level (Step 609).

Figure 10B:
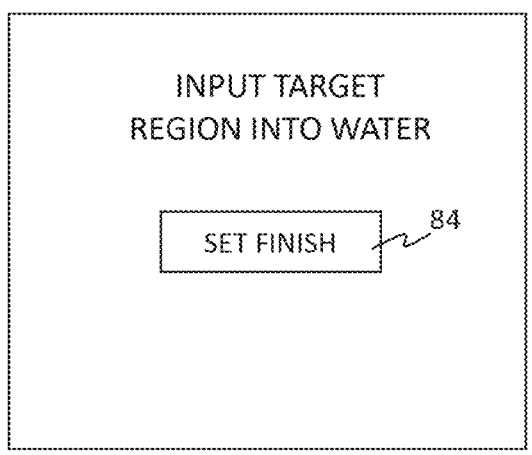

In a case where the dissolved oxygen level is lower than the set value in Step 608, the procedure proceeds to Step 610, and the controller 4 displays information of urging to insert and set the target region 10 into the water from the opening 10 of the water tank 20, for example, like a screen in FIG. 10(b) on the display unit 70 (Step 610). The user inserts the target region 10 (for example, the breast) into the water from the opening 10 of the water tank 20. Since the mesh 6 is disposed on the opening 10, the target region 10 is inserted into the water tank 20 while pushing the mesh 6 in the water tank 20 and deforming the mesh 6. The mesh is in a close contact state with the surface of the target region 10.

When the target region 10 is set in the water tank 20 (Step 611), the controller 4 executes scanning for detecting bubbles and obtains an initial value of a bubble index (bubble index $_{pre}$) (Step 612). In Step 611, as a method in which the controller 4 checks that the target region 10 is set in the water tank 20, it is possible to use a method of detecting that the user presses a set finish button 84 on a display screen in FIG. 10(b) of the display unit 70. In addition, similar to Step 603, in a case where the controller 4 causes the transmitting/receiving circuit 83 to transmit and receive the ultrasound in the water tank 20 and detects the shape of the target region 10 different from the water surface, the controller determines that the target region 10 is set.

The scanning for detecting bubbles in Step 612 is described in detail with reference to the flowchart in FIG. 9. The controller 4 controls the transmission/reception-unit driving unit 102 and disposes the transducer array 92 at a predetermined initial position (Step 701). The controller 4 controls the transmitting unit 86 and the receiving unit 87 of the transmitting/receiving circuit 83, causes one or more transducers 1 of the transducer array 92 to transmit the ultrasonic signal S21 toward the target region 10, and causes another transducer 1 to receive the ultrasonic signal (Step 702). The controller 4 receives the amplified received signal S41. This is repeatedly performed until the ultrasonic signals S21 are transmitted from all of the transducers 1 in order, while the transducer that transmits the ultrasonic signal S21 is changed. The computing unit 54 in the controller 4 calculates a delay time taken for the ultrasonic signal S21 transmitted from a certain transducer 1 to be reflected from the surface of the target region 10 and, then, to be received by another transducer 1, thereby, calculating the shape of the target region 10 (Step 703). In a case where there is unevenness on the calculated shape (contour) of the target region 10, the bubbles are attached on the surface of the target region 10 and the shape of the bubbles is detected. Hence, the controller 4 calculates a degree of unevenness of the calculated shape (contour) of the target region 10 by using a predetermined expression or the like and sets the degree of unevenness as the bubble index (Step 704).

In addition, by using a fact that more harmonic components are generated due to the bubbles than the target region 10, in Step 703, the controller 4 detects a harmonic component (for example, a second harmonic wave) included in the ultrasonic signal S21 reflected from the surface of the target region 10, instead of detecting the shape of the target region, obtains a ratio of the harmonic components to the fundamental components (ultrasonic signals S21), and may set the ratio as the bubble index.

In a case where the bubbles are attached on the surface of the target region 10, the bubbles have a significant influence, and thus measurement accuracy is degraded when the target region 10 is measured as it is. Therefore, the controller 4 operates the motor 72 of the rotating mechanism 7 of the mesh frame 61 and rotates the mesh frame 61 by a predetermined angle. For example, the mesh frame 61 is rotated by the predetermined angle in a clockwise direction. Then, it is more preferable that the mesh frame 61 is further rotated by the predetermined angle in a counterclockwise direction. The rotation may be performed a plurality of times. Since the mesh 6 supported by the mesh frame 61 moves due to the rotation so as to slide over the surface of the target region 10 in a state in which the mesh is in contact with the surface of the target region 10, the bubbles attached to the surface of the target region 10 are rubbed off by the mesh 6, are separated from the target region 10 into the water, and move to the water surface. Since the through-hole 73 for releasing the bubbles is disposed in the vicinity of the water surface, the bubbles reaching the vicinity of the water surface are released to the outside from the through-hole 73.

Figure 9:
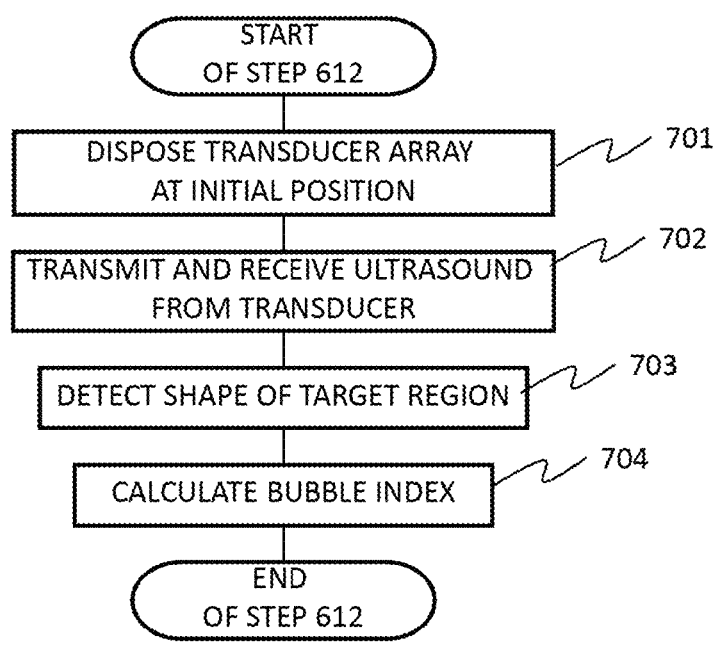
FIG. 9 is a flowchart illustrating an operation of the controller 4 of the second embodiment.

Then, the controller 4 performs scanning for detecting bubbles in FIG. 9 which is similar to that in Step 612 and calculates a bubble index (bubble index $_{post}$) of the target region 10 (Step 614), which is obtained after the bubbles are removed due to the rotation of the mesh 6 in Step 613. The controller 4 counts up times Nbd of performing the scanning for detecting bubbles (Step 615) and, then, calculates a difference between the bubble index $_{pre}$ obtained before the current rotation of the mesh 6 and the bubble index $_{post}$ after the rotation. In a case where the calculated difference is larger than the set value, the bubbles that can be removed still remain, and thus the procedure proceeds to Step 618 (Step 616). In Step 618, in a case where the times Nbd of performing the scanning for detecting bubbles is smaller than a threshold value, the procedure returns to Step 613 again. The controller 4 rotates the mesh 6, then, calculates the bubble index $_{post}$, and counts up the times Nbd of performing the scanning for detecting bubbles (Steps 613 to 615). The controller calculates a difference between the previously calculated bubble index $_{post}$ as the bubble index $_{pre}$ and a currently calculated bubble index $_{post}$. In a case where the obtained difference is larger than the set value, and the bubbles that can be removed still remain, the procedure proceeds to Step 618, and Steps 613 to 615 are repeatedly performed so as to remove the bubbles. In addition, in a case where the difference between the bubble index $_{pre}$ and the bubble index $_{post}$ is smaller than a predetermined value in Step 616, an amount of the bubbles to be removed is smaller than a predetermined amount, and the procedure proceeds to Step 617. In addition, in a case where the difference between the bubble index $_{pre}$ and the bubble index $_{post}$ is larger than the set value but the times Nbd of performing the scanning for detecting bubbles is larger than the threshold value in Step 618, an alarm is displayed on the display unit 70, and the measurement is ended (Step 619).

The controller 4 reduces the pressure in the water tank 20 by a predetermined amount in Step 617. Specifically, the controller 4 instructs the water regulator 34 to open the on-off valve 32 so as to move water from the water tank 20 to the deaerated water reservoir 33 by a predetermined amount. The movement of the water may be performed by using the own weight of the water or by using a pump function of the deaerated water reservoir 33. The pressure sensor 35 detects the pressure of the water in the deaerated water reservoir 33 and outputs the detection result to the controller 4. The controller 4 controls the water regulator 34 such that the pressure has a predetermined value. In this manner, since the pressure in the water tank 20 is reduced in a state in which the opening 11 of the water tank 20 is blocked by the target region 10, the pressure in the water tank 20 becomes the negative pressure with respect to the pressure in the outside, the pulling force F is uniformly applied to the surface of the target region 10 in the normal direction, the shape of the target region 10 approaches a predetermined shape, and such a state is maintained. For example, in a case of the breast, it is possible to decrease the influence of the position or the direction of the breast on the shape of the breast when the breast is inserted into the container by reducing the pressure and to approach the predetermined shape of the breast. The through-hole 73 for releasing the bubbles is closed by closing the valve (not illustrated), during the reduction of the pressure.

When the pressure in the water tank 20 is reduced by the predetermined amount, the procedure proceeds to Step 620, and the controller 4 checks whether the user can allow a state in which the current pressure is applied to the target region 10 (Step 620). In a case where the user can allow the state, the shape of the target region 10 is detected by the transmission and reception of the ultrasound (Step 621). The detection of the shape of the target region 10 in Step 621 is performed in the similar manner in Steps 701 to 703 in FIG. 9. In a case where the detected shape is not present within a predetermined range, the procedure returns to Step 617, and the controller 4 reduces the pressure in the water tank 20 by the predetermined amount. This operation is repeatedly performed until the shape of the target region 10 can reach the predetermined range (Steps 617 to 623). In a case where the shape of the target region 10 reach the predetermined range, the controller 4 causes the valve 32 to come into the closed state and maintains the pressure in the water tank 20 in this state, and the procedure proceeds to next Step 624. In Step 621, in the case where the target region 10 is the breast, it is possible to determine whether the detected shape is present within the predetermined range, by determining whether or not the rate between the diameter of the opening 11 of the water tank 20 (or, a diameter of a desired proximal portion of the breast in the opening 11) and the distance from the opening 11 to the distal end of the breast is present within the predetermined range. As the pressure is reduced, the distance from the opening 11 to the distal end of the breast increases, and thus it is possible to cause the shape of the breast to reach the predetermined shape.

In Step 620, for example, in a case where the user presses the pressure reduction stop button 82a in FIG. 10(a) so as to inform the controller 4 that the user cannot allow the current pressure, the procedure proceeds to Step 622, and the controller 4 controls the water regulator 34 and the deaerated water reservoir 33 so as to increase the amount of water by a predetermined amount and decrease the reduction of the pressure, and then closes the valve 32. The shape of the target region 10 does not reach the predetermined shape, and the procedure proceeds to next Step 624.

In Step 624, the controller 4 detects the central position (for example, the distal end position of the breast) from the shape of the target region 10 which is detected in Step 621 and determines whether or not the central position is present within a predetermined range. In a case where the central position of the shape of the target region 10 is out of the predetermined range, the moving mechanism 8 moves the mesh frame 61 by a predetermined amount in the reverse direction to the direction in which the central position is shifted (Step 625). Specifically, the controller 4 causes the drive unit 8b to lift the engagement portion 8a of the moving mechanism 8 such that the engagement portion engages with the edge of the mesh frame 61. Then, the engagement portion 8a is caused to move in parallel with the opening 11 in the reverse direction to the direction in which the central position of the target region 10 is shifted, and thereby the mesh frame 61 is moved. In this manner, since the mesh 6 moves together with the mesh frame 61, it is possible to correct the central position of the target region 10 by the mesh 6. This operation is repeatedly performed until the central position moves to the inside of the predetermined range (Steps 621 to 625).

When the central position enters the predetermined range, the controller 4 properly measures the target region 10 by transmitting and receiving the ultrasound (Step 626). Through Steps 601 to 625, the bubbles are removed from the surface of the target region 10, the shape reaches the shape within the predetermined range or the shape is maintained in an approaching state, and the central position is present within the predetermined range. Therefore, it is possible to perform proper measurement with high accuracy. Specifically, the controller 4 controls the transmitting/receiving circuit 83, thereby causing one or more transducers 1 of the transducer array 92 to transmit the ultrasonic signal S21 and causing another transducer 1 to receive the ultrasonic signal S21 penetrating and/or reflected from the target region 10 (Step 626). This is repeatedly performed until the ultrasound is transmitted from all of the transducers 1 while the transducer 1 is changed. Next, the controller 4 causes the transmission/reception-unit driving unit 102 to move the position of the transducer array 92 to a predetermined position and similarly performs the transmission from and reception to the transducers 1. This is performed at positions by moving the transducer array 92 at a predetermined pitch. After the measurement, the controller 4 opens the valve 32 or opens the through-hole 73 for releasing bubbles so as to perform leaking, and the pressure in the water tank 20 returns to the atmospheric pressure.

The computing unit 54 of the controller 4 computes the amplified received signal S41 obtained from the transmitting/receiving circuit 83 by using the parameter value that is stored in the parameter storing unit 19, thereby calculating the shape of the target region 10 and the physical property value such as the sound speed distribution or the attenuation distribution in the target region 10 (Step 627). The controller 4 stores the calculated shape/sound speed distribution/attenuation distribution in the storage unit 52. The image generating unit 51 generates the image showing the shape, the sound speed distribution, or the attenuation distribution which is calculated by the computing unit 54 (Step 628).

The difference detecting unit 53 of the controller 4 reads, from the storage unit 52, the data or the image of the shape/sound speed distribution/attenuation distribution in the same subject 100, which is obtained in the previous measurement, compares the data or the image obtained in the previous measurement with the data and the image obtained in the current measurement, and detects a difference therebetween (Step 629).

Figure 10C:
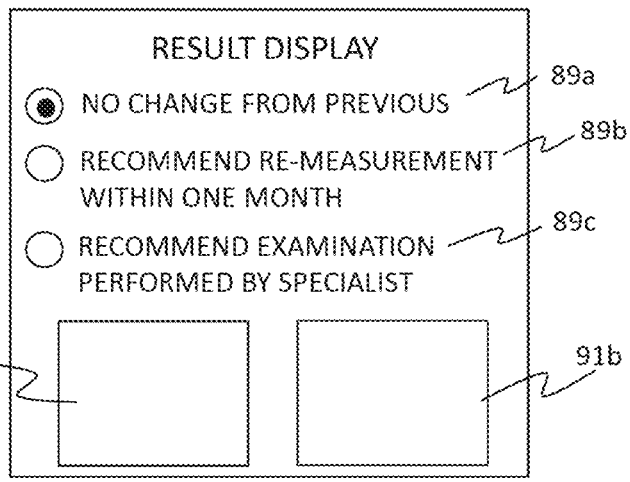

In a case where the detected difference is present within the predetermined range, for example, the controller 4 displays the information for notifying the user that there is no change from the previous measurement, like a display 89a in FIG. 10(c) on the display unit 70. The detected difference is out of the predetermined range; however, when the size of the difference does not exceed a predetermined value, a display of recommending re-measurement in near days (for example, within one month) is displayed like a display 89b in FIG. 10(c). This is because there is a possibility of a difference due to an error or the like in the shapes from the previous measurement. In addition, in a case where the difference is out of the predetermined range and the size of the difference is equal to or larger than the predetermined value, a display of recommending an examination performed by a specialist is displayed like a display 89*c* in FIG. 10(*c*). In addition, the controller 4 can display an image of the shape/sound speed distribution/attenuation distribution in an image display region 91*a* of a display screen of the display unit 70 and can display the data of the shape/sound speed distribution/attenuation distribution as numerical values in a data display region 91*b* of the display screen (Step 630). In addition, in a case where the user wants to keep an image or data thereof, it is possible to give the user by printing the image or the data or writing the data in a predetermined external recording medium, and it is possible to perform transmission to the hospital of the specialist via a communication line.

The controller 4 end the measurement, even at any time point between Steps 601 to 630, in a case where a signal of pressing an emergency stop button 82*b* (FIG. 10(*a*)) by the user is received.

According to the ultrasonic imaging device of the second embodiment, it is possible to maintain the shape close to the predetermined shape by reducing the pressure when the target region such as the breast or the like is inserted into the water tank. In addition, the bubbles on the surface of the target region can also be removed. Hence, since the same shape is maintained every time such that it is possible to perform measurement by the ultrasound with high accuracy, it is possible to detect the difference in image or data due to a minute difference in the appearance of the breast or internal tumor masses with time with high accuracy by comparing the results of the current measurement with the results of the previous measurement. Hence, it is possible to assist the diagnosis by a doctor.

In addition, the ultrasonic imaging device of the embodiment enables the user to perform self examination without meeting a doctor. Hence, the user can easily perform the examination of oneself by installing the device at a position such as a sports facility or a public bath other than the hospital. In this manner, it is possible to increase an opportunity of the examination. In addition, in a case where the difference between the current examination and the previous examination is large, it is possible to recommend the examination performed by the specialist and to transmit the data or the like. Therefore, this leads to early detection of a disease such as the breast cancer and is beneficial to the user.

Third Embodiment

An ultrasonic imaging device of a third embodiment is described with reference to FIGS. 11(*a*) to 11(*d*). The embodiment differs from the first and second embodiments in that a mesh, to which markers 111 are attached at predetermined intervals, is used as the mesh 6. A mesh made of a material having the low sound attenuation is used as the mesh 6 described in the first embodiment; however, the marker 111 is a fine object made of a material having higher sound attenuation than that of the target region 10. The marker may have any shape, or it is possible to use a spherical marker 111, for example. The interval of the markers 111 on the mesh 6 is set to an interval by which the ultrasonic signal S21 reaches the target region 10 without interference.

Figure 7:
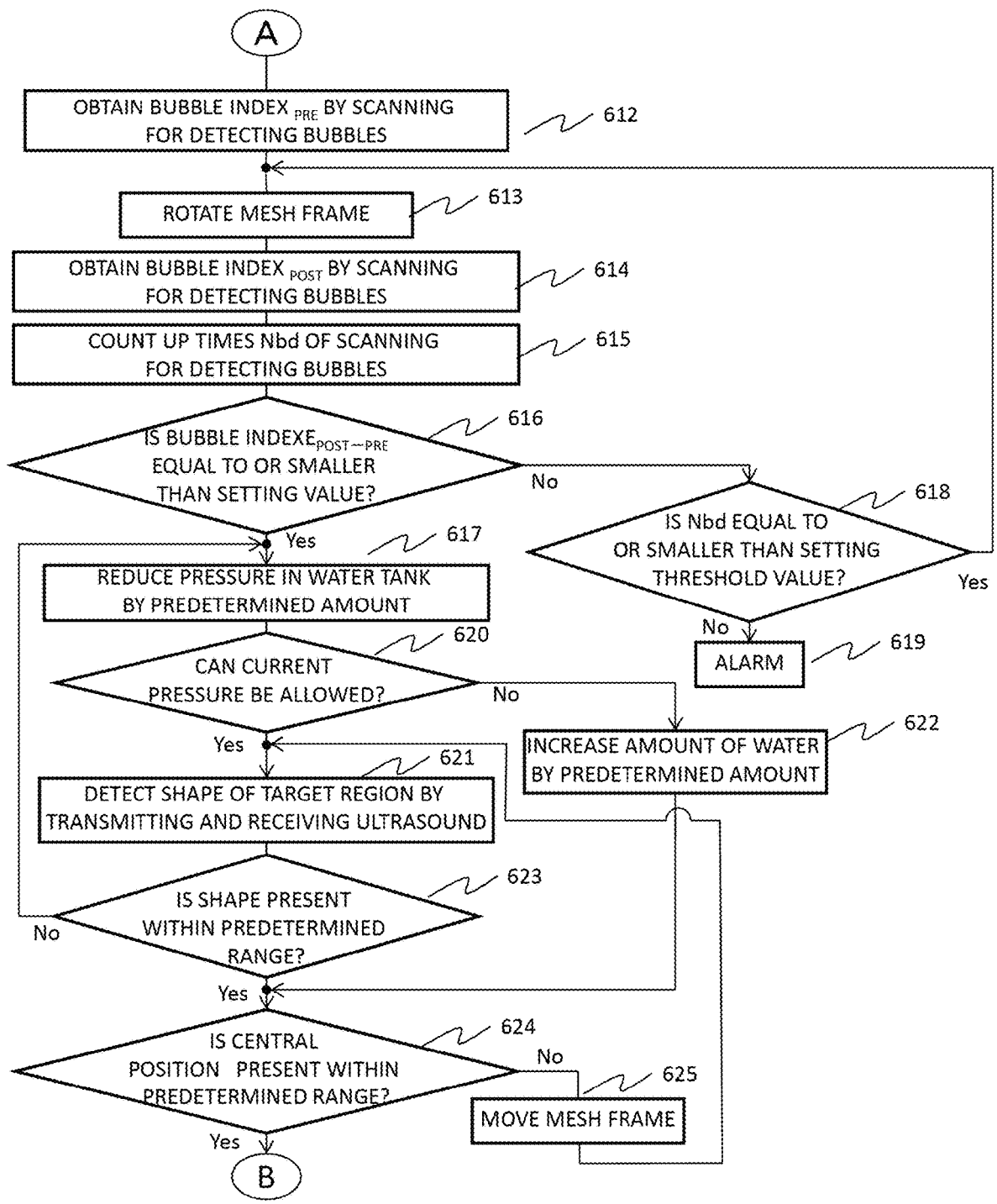
FIG. 7 is a flowchart illustrating an operation of the controller 4 of the second embodiment.
Figure 8:
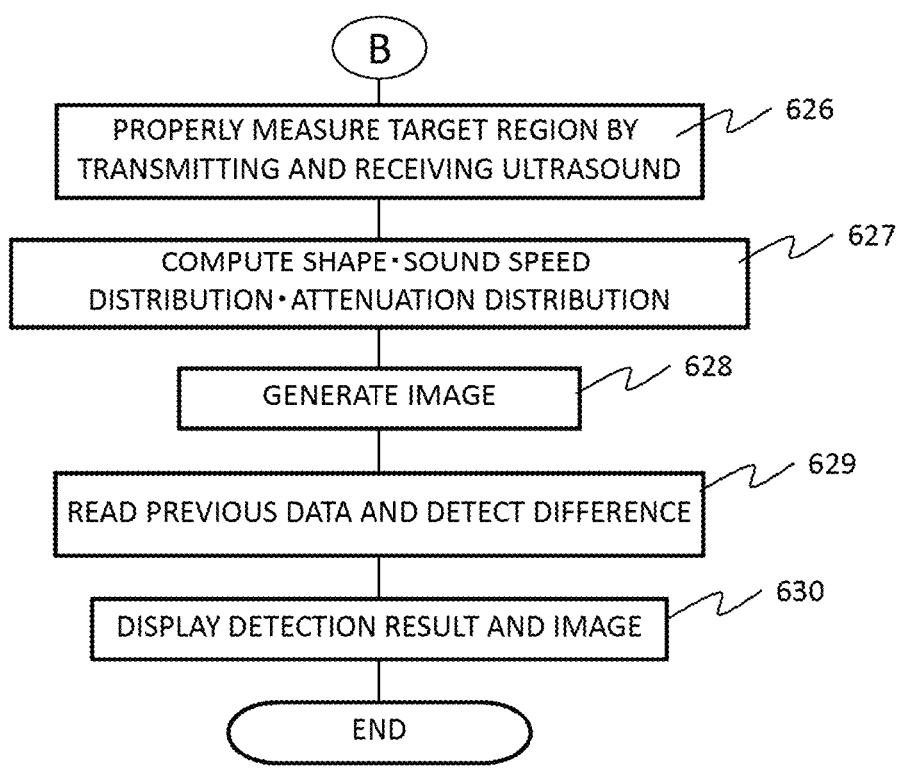
FIG. 8 is a flowchart illustrating an operation of the controller 4 of the second embodiment.

In the embodiment, since the markers 111 are arranged, the controller 4 detects the positions of the markers 111, instead of detecting the shape of the target region by transmitting and receiving the ultrasound in Step 621 in FIG. 7, and thereby it is possible to roughly detect the surface shape of the target region 10. Since the marker 111 has sound attenuation higher than that of the target region 10, and the shape thereof is also a predetermined shape, the controller 4 can easily detect the positions of the markers 111, compared to a case where the surface shape of the target region 10 is detected. Hence, it is possible to shorten a computing time of the computing unit 54 in Step 621, and it is possible to shorten a time taken in Steps 621 to 625 in which the shape of the target region 10 approaches the predetermined shape.

The other configurations and operations are the same as those in the first and second embodiments, and thus the description thereof is omitted.

In addition, the example in which the marker 111 is detected by transmitting and receiving the ultrasound is described in the third embodiment; however, the embodiment is not limited to this example, and it is possible to optically detect the marker 111. In this case, the material of the marker 111 does not have different sound attenuation from the target region 10, but a material having an optical property such as reflectance different from that of the target region 10 is used. In this manner, the mesh 6 is irradiated with light, reflected light is detected, and thereby it is possible to detect the position of the marker 111.

Fourth Embodiment

An ultrasonic imaging device of a fourth embodiment is described with reference to FIGS. 12 to 14.

The device of the fourth embodiment differs from the devices of the first and second embodiments in that the mesh frame 61 supporting the mesh 6, the rotating mechanism 7 that rotates the mesh frame 61, and the moving mechanism 8 that moves the mesh frame 61 have different structures. FIGS. 12(*a*) and 12(*b*) are sectional and top diagrams of the water tank 20 that has the rotating mechanism 7 and the moving mechanism 8. FIGS. 13(*a*) and 13(*b*) are top and sectional diagrams of the mesh frame 61. FIG. 14 is a sectional diagram illustrating a state in which the mesh frame 61 is mounted on the water tank 20.

Figure 12A:
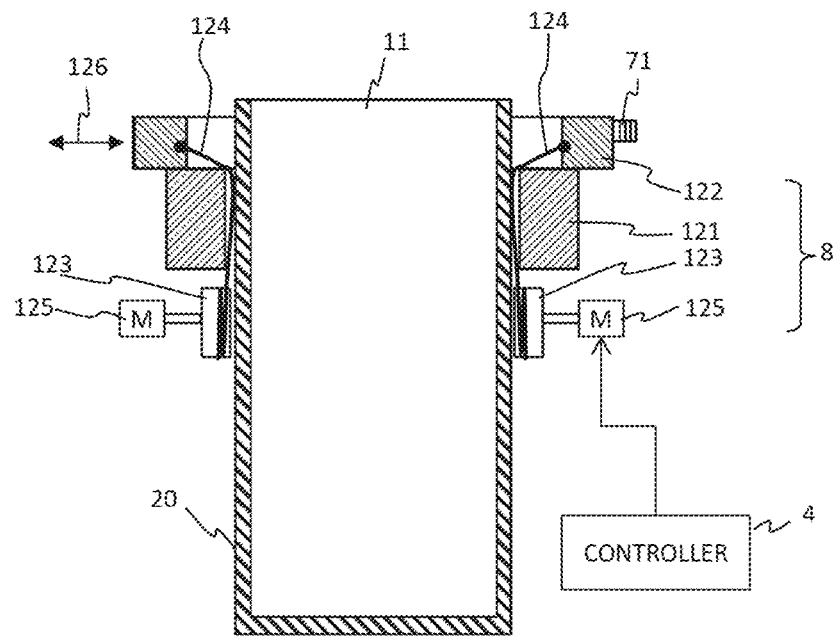
FIGS. 12A and 12B are sectional and top diagrams of a water tank 20 that has a rotating mechanism 7 and a moving mechanism 8 of a fourth embodiment.
Figure 12B:
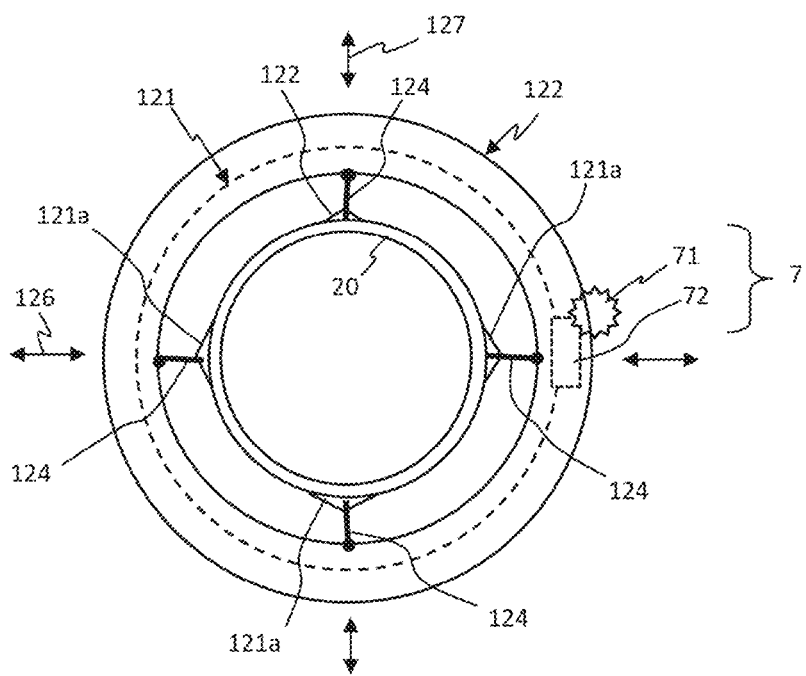

As illustrated in FIGS. 12(*a*) and 12(*b*), in the embodiment, the moving mechanism 8 includes a ring-shaped retainer 121 fixed to the outer circumference of the water tank 20 having the circular cylinder shape, a ring-shaped mesh frame retainer 122 mounted on the retainer 121, four wire reels 123 fixed to the outer circumference of the water tank 20 at 90° intervals at a position lower than the retainer 121, and four motors 125 connected to the four wire reels 123, respectively. The mesh frame retainer 122 is not fixed to the retainer 121 but is only mounted on the top surface of the retainer 121 and is movable over the top surface of the retainer 121 in parallel with the opening 11. One end of the wire 124 is fixed to an inner wall of the mesh frame retainer 122, and the wires 124 are fixed at four positions, respectively. An inner wall of the retainer 121 is provided with notches 121*a* in a thickness direction above the wire reels 123, respectively. The other end of the wire 124 is wound around the wire reel 123 through the notch 121*a*. Hence, under the control performed by the controller 4, the motor 125 rotates one of a pair of wire reels 123 facing each other in a direction of winding the wire 124 and rotates the other wire reel in a direction of loosening the wire 124, and thereby it is possible to move the mesh frame retainer 122 in a direction 126 in which the two wire reels 123 face each other. Similarly, a pair of wire reels 123 disposed in a direction 127, which is orthogonal to the pair of wire reels 123 described above, is similarly rotated, and thereby it is possible to move the mesh frame retainer 122 in the direction 127.

In addition, a rotatable driving gear 71 is disposed in a part of the outer circumference of the mesh frame retainer 122, and the motor 72 that rotates the driving gear 71 is disposed inside the mesh frame retainer 122.

Figure 13A:
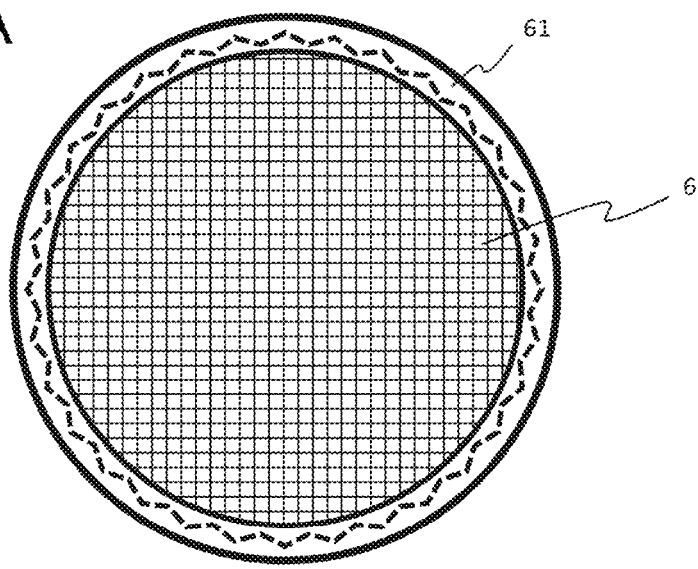
FIGS. 13A and 13B are top and sectional diagrams of a mesh frame 61 of the fourth embodiment.
Figure 13B:
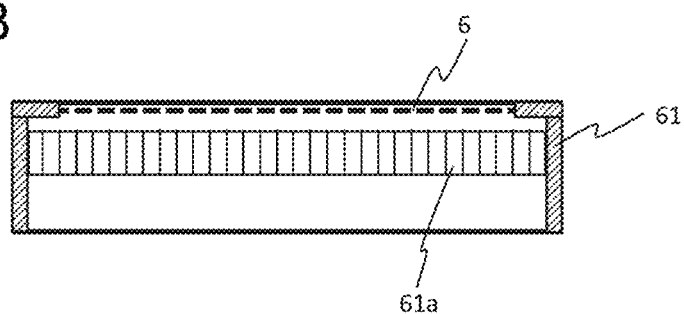

On the other hand, as illustrated in FIGS. 13(*a*) and 13(*b*), the mesh frame 61 has a circular cylinder shape and a gear 61*a* intermeshing with the driving gear 71 is provided on the inner wall.

Figure 6:
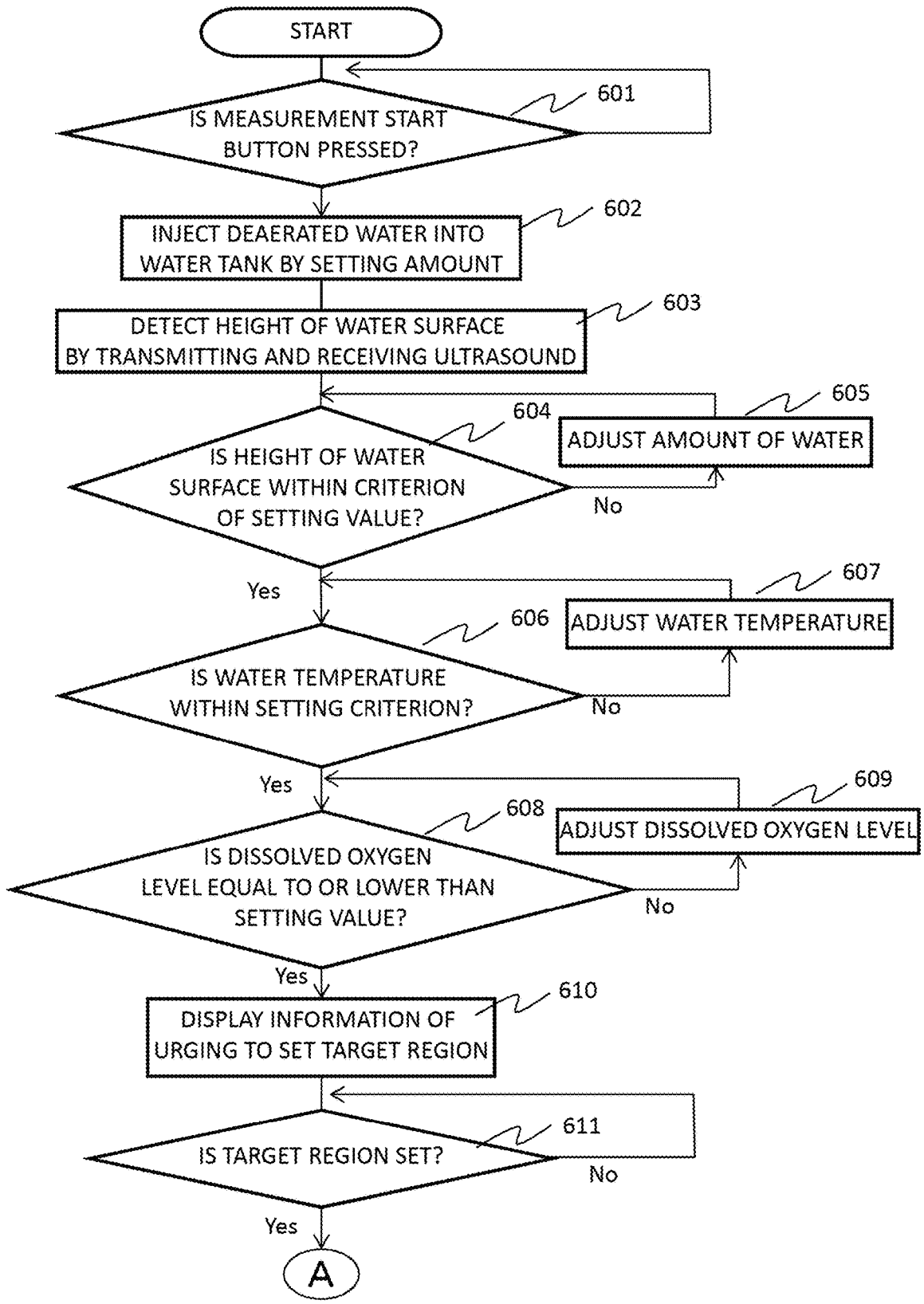
FIG. 6 is a flowchart illustrating an operation of a controller 4 of the second embodiment.
Figure 14:
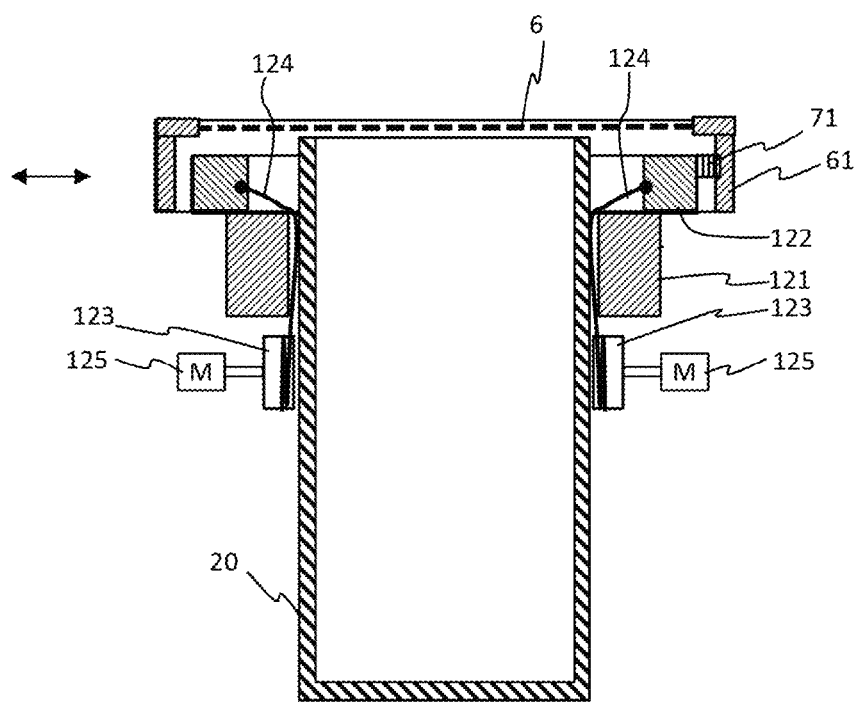
FIG. 14 is a sectional diagram illustrating a state in which the mesh frame 61 is mounted on the water tank 20 of the fourth embodiment.

Hence, as illustrated in FIG. 14, the mesh frame 61 covers the mesh frame retainer 122, and the driving gear 71 and the gear 61*a* of the inner wall of the mesh frame 61 intermesh with each other, and thereby the mesh frame retainer 122 can support the mesh frame 61. In this state, Step 601 in FIG. 6 is started. When the target region 10 is inserted into the water tank 20 in Step 611, the mesh 6 that is supported by the mesh frame 61 is pushed into the water tank 20 along with the target region 10, similarly in FIG. 1(*b*).

In Step 613 in FIG. 7, the controller 4 can rotate the mesh frame 61 by a predetermined angle when the motor 72 of the rotating mechanism 7 is rotated and the driving gear 71 is rotated. In this manner, it is possible to remove the bubbles on the target region 10.

In addition, in Step 625 in FIG. 7, the controller 4 drives the motor 125 of the moving mechanism 8, winds the wire 124 around one of the pair of reels facing each other, and loosens the wire 124 around the other reel, and thereby the mesh frame retainer 122 moves in a horizontal direction in a state in which the mesh frame retainer supports the mesh frame 61. In this manner, since it is possible to move the mesh frame 61 in a predetermined direction, it is possible to correct the central position of the target region 10.

The other configurations and operations are the same as those in the first and second embodiments, and thus the description thereof is omitted. In addition, like the third embodiment, the mesh frame 61 can also hold the mesh 6 provided with the markers 111.

INDUSTRIAL APPLICABILITY

The present invention can be applied to the ultrasonic imaging device.

REFERENCE SIGNS LIST

1: transducer
2: transmission/reception unit
3: pressure reducing unit
4: controller
5: transmission/reception controller
6: mesh
7: rotating mechanism
8*a*: engagement portion
8*b*: drive unit
10: target region
11: opening
20: container (water tank)
51: image generating unit
52: storage unit
53: difference detecting unit
55: bed
56: opening
61: mesh frame
61*a*: gear
71: driving gear
72: motor
73: bubble releasing through-hole
83: transmitting/receiving circuit
95: signal line
100: subject
102: transmission/reception-unit driving unit
104: bed driving unit
121: retainer
121*a*: notch
122: mesh frame retainer
123: wire reel
124: wire
125: motor

The invention claimed is:

1. An ultrasonic imaging device comprising:
a container provided with an opening that is configured to receive a target region of a subject;
an ultrasound transceiver configured to transmit an ultrasonic signal to the target region when the target region is disposed in the container, and configured to receive a scattered ultrasonic signal from the target region disposed in the container;
a pressure valve configured to control a pressure in the container; and
a controller configured to control the pressure valve,
wherein the controller is configured to detect a shape of the target region after causing the pressure valve to reduce the pressure in the container by a predetermined pressure and determine whether or not the shape corresponds to a predetermined shape;
wherein the pressure valve is configured to control a surface state of the target region based on the control of the pressure in the containers;
wherein the container has an extensible mesh that is disposed to cover the opening;
wherein the extensible mesh is displaceable into a space in the container;
wherein a periphery of the mesh is held by a mesh frame;
the ultrasonic imaging device further comprising:
a rotating mechanism configured to rotate the mesh frame along a periphery of the opening of the container; and
a moving mechanism configured to move the mesh frame in at least one direction in a plane of the opening of the container.

2. The ultrasonic imaging device according to claim 1, wherein a space in the container is filled with a liquid, and the pressure valve is configured to discharge, to an outside of the container from a through-hole provided in the container, a part of the liquid with which the space in the container is filled.

3. The ultrasonic imaging device according to claim 1, wherein the controller is configured to cause the pressure valve to further reduce the pressure in the container in a case where the shape of the target region does not correspond to the predetermined shape.

4. The ultrasonic imaging device according to claim 1, wherein the controller is configured to detect the shape of the target region, based on the scattered ultrasonic signal.

5. The ultrasonic imaging device according to claim 1, further comprising:
an image generating unit configured to calculate an image of the target region based on the scattered ultrasonic signal;
a storage unit configured to store the image; and
a difference detecting unit configured to obtain a difference obtained by comparing the image that is currently calculated by the image generating unit to an image calculated in the past by the image generating unit.

6. The ultrasonic imaging device according to claim 1, wherein the mesh is attachable to and detachable from the opening.

7. The ultrasonic imaging device according to claim 1, further comprising:
a controller configured to control the ultrasound transceiver and the rotating mechanism,
wherein the space in the container is filled with a liquid, and
wherein the controller detects whether or not bubbles are present on a surface of the target region and causes the rotating mechanism to rotate the mesh frame in a case where an amount of bubbles, which is equal to or larger than a predetermined amount, is present on the surface of the target region.

8. The ultrasonic imaging device according to claim 7, wherein the controller detects the bubbles on the surface of the target region, based on a received signal obtained by causing the ultrasound transceiver to transmit the ultrasonic signal and receive the scattered ultrasonic signal.

9. The ultrasonic imaging device according to claim 1, further comprising:
a controller configured to control the ultrasound transceiver and the moving mechanism,
wherein the controller obtains a position of the target region with respect to the container and causes the moving mechanism to move the mesh frame in a case where the position is out of a predetermined range.

10. The ultrasonic imaging device according to claim 1, further comprising:
a bed on which the subject is mounted,
wherein the bed is provided with a recessed portion or a through-hole for inserting the target region of the subject,
wherein the container is disposed in the recessed portion or the through-hole, and
wherein the ultrasound transceiver has a ring-shaped transducer array that transmits the ultrasonic signal and receives the scattered ultrasonic signal and a moving mechanism configured to move the ring-shaped transducer array in a central axis direction of the container.

11. The ultrasonic imaging device according to claim 1, wherein the control device is configured to determine that the shape corresponds to the predetermined shape when a ratio of a diameter and a length is within a predetermined range.

12. An ultrasonic transmission and reception method, comprising:
inserting a target region of a subject into a container provided with an opening and covering the opening with the target region;
holding the target region in the container by reducing a pressure in the container;
transmitting an ultrasonic signal to the target region in the container and receiving a scattered ultrasonic signal from the target region; and
detecting a shape of the target region after causing a pressure valve to reduce the pressure in the container by a predetermined pressure, and determining whether or not the shape corresponds to a predetermined shape;
wherein the container has an extensible mesh that is disposed to cover the opening;
wherein the extensible mesh is displaceable into a space in the container;
wherein a periphery of the mesh is held by a mesh frame;
rotating the mesh frame along a periphery of the opening of the container; and
moving the mesh frame in at least one direction in a plane of the opening of the container.

* * * * *